(12) United States Patent
Yeates et al.

(10) Patent No.: US 6,756,039 B1
(45) Date of Patent: Jun. 29, 2004

(54) SELF ASSEMBLING PROTEINS

(75) Inventors: Todd O. Yeates, Agoura Hills, CA (US); Jennifer Padilla, Los Angeles, CA (US); Chris Colovos, Thousand Oaks, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/564,710

(22) Filed: May 3, 2000

Related U.S. Application Data (60) Provisional application No. 60/133,470, filed on May 10, 1999.

(51) Int. Cl.$^7$ .............................................. A61K 39/00
(52) U.S. Cl. ...................... 424/192.1; 435/6; 435/69.1; 435/325; 435/91; 435/170; 435/171; 435/172.3; 435/240.2; 435/252.3; 435/254; 435/287; 536/27; 530/324; 530/300; 530/351; 530/350
(58) Field of Search .......................... 435/325, 6, 69.7, 435/91, 170, 171, 172.3, 240.2, 252.3, 254, 257, 69.1; 530/350, 351, 402, 412, 324, 300; 536/27; 424/192.1

(56) References Cited

U.S. PATENT DOCUMENTS

| | | | | |
|---|---|---|---|---|
| 5,008,373 A | * | 4/1991 | Kingsman et al. | 530/350 |
| 5,573,925 A | * | 11/1996 | Halazonetis | 435/69.7 |
| 5,877,279 A | * | 3/1999 | Goldberg | 530/350 |
| 6,242,570 B1 | * | 6/2001 | Sytkowski | 530/350 |

OTHER PUBLICATIONS

Ajayan et al. (1997). "Nanometre–size tubes of carbon" *Rep. Prog. Phys.*, vol. 60: 1025–1062.

Chui et al. (1999). "A chemically functionalizable nanoporous material [$Cu_3(TMA)_2(H_2O)_3$]$_n$," *Science*, vol. 283: 1148–1150.

Collier et al. (1998). "Nanocrystal superlattices" *Annu. Rev. Phys. Chem.*, vol. 49: 371–404.

Ghadiri et al. (1993). "Self–assembling organic nanotubes based on a cyclic peptide architecture" *Nature*, vol. 366: 324–327.

Iijimi et al. (1991). "Helical microtubules of graphitic carbon" *Nature*, vol. 354: 56–58.

Kroto et al. (1987). "The stability of the fullerenes of $C_n$, with n=24, 28,32,36,50,60 and 70." *Nature*, vol. 329(8): 529–5531.

Li et al. (1999). "Supertetrahedral sulfide crystals with giant cavities and channels" *Science*, vol. 283: 1145–1147.

Rao et al. (1996). "Fullerenes and carbon nanotubes" *Current Opinion in Solid State & Materials in Science*, vol. 1: 279–284.

Seeman (1999). "DNA engineering and its application nanotechnology" *Tibtech*, vol. 17: 437–443.

Stange et al. (1998). "Self–organizing molecular works" *Biophysical Chemistry*, vol. 72: 73–85.

Wukovitz et al. (1995). "Why protein crystals favour some space–groups over others" *Nature Structural Biology*, vol. 2(12): 1062–1067.

* cited by examiner

*Primary Examiner*—Karen Cochrane Carlson
*Assistant Examiner*—Hope A. Robinson
(74) *Attorney, Agent, or Firm*—Bret E. Field; Bozicevic, Field & Francis LLP (57) ABSTRACT

Novel fusion proteins capable of self-assembling into regular structures, as well as nucleic acids encoding the same, are provided. The subject fusion proteins comprise at least two oligomerization domains rigidly linked together, e.g. through an alpha helical linking group. Also provided are regular structures comprising a plurality of self-assembled fusion proteins of the subject invention, and methods for producing the same. The subject fusion proteins find use in the preparation of a variety of nanostructures, where such structures include: cages, shells, double-layer rings, two-dimensional layers, three-dimensional crystals, filaments, and tubes.

27 Claims, 6 Drawing Sheets

Figure 1

Two examples of architectures that can be designed
by fusing a dimeric component to a trimeric component

Experimental verification of a designed protein cage

An atomic model of the designed protein cage
(diameter approximately 15nm)

Figure 4

Electron micrographs of a designed self-assembling
protein filament

Fig. 5a     Fig. 5b

Atomic structure of a designed self-assembling protein filament

Fig. 6

SELF ASSEMBLING PROTEINS

CROSS REFERENCE TO RELATED APPLICATIONS

Pursuant to 35 U.S.C. §119 (e), this application claims priority to the filing date of the U.S. Provisional Patent Application Serial No. 60/133,470 filed May 10, 1999, the disclosure of which is herein incorporated by reference.

ACKNOWLEDGMENT OF GOVERNMENT SUPPORT

This invention was made with Government support under Grant No. DE-FGO3-87ER60615 awarded by the Department of Energy and Grant No. GM31299 awarded by the National Institute of Health. The Government has certain rights in this invention.

INTRODUCTION

1. Technical Field

The field of this invention is nanotechnology and biomaterials.

2. Background of the Invention

A central goal of nanotechnology research is to design and fabricate novel materials with sizes or length scales in the nanometer range. These materials fall into a variety of architectural classes, such as compact clusters, hollow shells, tubes, two-dimensional layers, and three-dimensional molecular networks. In recent years, a wide combination of chemical building blocks and synthetic strategies have been investigated. Numerous specific methods have produced interesting new materials, but a single general strategy for fabricating materials having many different architectures and symmetries has not been developed. Furthermore, most of the recent work has focused on inorganic and organic synthetic materials as building blocks, while biological molecules such as proteins offer some special advantages that have not yet been exploited. As such, there is continued interest in the development of new materials and systematic methods for producing nanostructures, especially using biological macromolecules Relevant Literature Various nanostructures and methods for their preparation are described in: Collier, et al., Ann. Rev. Phys. Chem. (1998) 49: 371–404 (compact clusters); Rao, et al., Current Opinion in Solid State and Materials Sci. (1996) 1:279–284 and Kroto, Nature (1987) 329:529 (hollow shells); Iijima, Nature (1991)354:56–58, Ghadiri, Nature (1993) 366:324–327 and Ajayan et al., Reports on Progress in Physics (1997) 60:1025–1062 (tubes); Stange, et al., Biophys. Chem. (1998) 72:73–85 (molecular networks); and Li, et al., Science (1999) 283: 1145–1147; Seeman, Trends in Biotechnology (1999)) 11:437–443 (DNA); and Chui, et al., Science (1999) 283:1148–1150 (two-dimensional layers). Also of interest is: Wukowitz et al., Nature Struct. Biol. (1995) 2:1062–1067.

SUMMARY OF THE INVENTION

Novel fusion proteins capable of self-assembling into regular structures, as well as nucleic acids encoding the same, are provided. The subject fusion proteins comprise at least two oligomerization domains rigidly linked together, e.g. through an alpha helical linking group, where the oligomerization domains are derived from naturally occurring proteins. Also provided are regular structures comprising a plurality of self-assembled fusion proteins of the subject invention, and methods for producing the same, where the structures may be homogenous or heterogeneous with respect to their fusion protein components. The subject fusion proteins find use in the preparation of a variety of regular structures, where such structures include: cages, shells, double-layer rings, two-dimensional layers, three-dimensional crystals, filaments, and tubes.

BRIEF DESCRIPTION OF THE FIGURES

FIG. 2. Schematic illustrations for some self-assembling architectures. a) An octahedral cage assembles from a dimer-trimer chimera. b) An extended layer of molecules with p6 symmetry assembles from a dimer-trimer chimera.

FIG. 3. Characterization of the designed tetrahedral protein assembly. a) Equilibrium sedimentation shows that the major component has a molecular weight of approximately 540 kDa. b) Negatively stained electron micrographs show triangular footprints of the tetrahedral assemblies. The particle size is consistent with the design.

DESCRIPTION OF THE SPECIFIC EMBODIMENTS

Novel fusion proteins capable of self-assembling into regular structures, as well as nucleic acids encoding the same, are provided. The subject fusion proteins comprise at least two oligomerization domains rigidly linked together, e.g. through an alpha helical linking group. Also provided are regular structures comprising a plurality of self-assembled fusion proteins of the subject invention, and methods for producing the same. The subject fusion proteins find use in the preparation of a variety of nanostructures, where such structures include: cages, shells, double-layer rings, two-dimensional layers, three-dimensional crystals, filaments, and tubes.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Fusion Proteins

As summarized above, the subject invention provides novel fusion proteins that are capable of assembling under suitable conditions to produce regular structures. The fusion proteins of the subject invention are characterized by having at least two oligomerization domains covalently linked or fused together, typically through a rigid linking group. Generally, the oligomerization domains are derived from naturally occurring proteins. By naturally occurring protein is meant a protein that occurs in nature. The number of distinct oligomerization domains or components found in the subject fusion proteins may vary, but typically ranges from 2 to 4, usually from 2 to 3. In general, the subject fusion proteins have a molecular weight of at least about 5 kDa, usually at least about 10 kDA and more usually at least about 20 kDa, where the molecular weight may be as high as 300 kDa or higher, but generally, does not exceed about 200 kDa and usually does not exceed about 150 kDa. In the subject fusion proteins, any two individual components may be the same or different.

The oligomerization domains or components of the subject fusion proteins are derived from proteins that are capable of associating, generally under physiological conditions, with at least one identical protein to produce a structure of two or more identical proteins, e.g. a dimeric structure, a trimeric structure, and tetramaric structure, etc. Generally, each naturally occurring protein component of the subject fusion proteins is either: (a) a protein which naturally associates into a dimeric structure (i.e. it associates with an identical protein to produce a dimer); (b) a protein which naturally associates into a trimeric structure (i.e. it associates with two identical proteins to produce a trimer); or (c) a protein which naturally associates by way of dimeric or trimeric building blocks to form larger assemblies (e.g. tetramers or hexamers). The weight of each naturally occurring protein component or oligomerization domain of the subject fusion proteins may vary, but generally is at least about 2 kD usually at least about 5 kDa and more usually at least about 10 kDa, where the weight may be as high as 100 kDa or higher, but usually will not exceed about 50 kDa. A further general characterization of the oligomerization domains is that they typically include an alpha helical structure at one of their termini, i.e. at the amino or carboxy terminus.

Typically, the naturally occurring protein components that make up the subject fusion proteins are ones that naturally associate with identical proteins to produce dimeric or trimeric structures. Other proteins that self-assemble into larger complexes such as tetramers and hexamers by way of dimeric and trimeric building blocks are also useful. Specific proteins of interest with known three-dimensional structures that naturally associate into oligomeric structures include those dimers and trimers and other oligomers listed in the publically available Protein Data Bank, described in Abola et al., Meth. Enzymol. (1997) 277:556–571, and the like. A critical feature of the subject fusion proteins is that the two or more naturally occurring protein components are rigidly joined to each other in a manner such that the orientation in space of each component relative to the other(s) in the fusion protein is relatively static and can be anticipated in advance based on the known structures of the components. Typically, the protein components of the subject fusion proteins are joined to each other through a rigid linking group that is capable of providing the requisite static orientation of the disparate components of the fusion protein. The length of the rigid linking group may vary depending on the desired overall geometry of the fusion protein, as described infra.

Generally, the linking group has a length ranging from about 1.5 Å to 48 Å, usually from about 6 Å to 30 Å and more usually from about 6 Å to 20 Å. As such, the number of residues in the linking group generally ranges from about 1 to 35, usually from about 2 to 20 and more usually from about 4 to 15.

Any linking group capable of providing the requisite static orientation of the disparate components of the fusion protein may be employed. Of particular interest in many embodiments is the use of a linking group that comprises an alpha helical structure. In other words, the linking group includes a sequence of amino acid residues which is prone to forming an alpha helix. A variety of such sequences are known and include long alpha helices found in the protein structure database such as the helix in the ribosomal protein L9 (PDB code 1div). Alternatively, it is understood that certain amino acid types tend strongly to adopt an alpha helical configuration, and the linker may be designed to contain amino acids with this tendency.

A critical feature of the subject fusion proteins is that they are capable of participating in a self-assembly process under suitable conditions to produce a regular, defined structure of a plurality of fusion proteins. By plurality of fusion proteins is meant at least about 2, but the number of individual fusion proteins in a particular structure is often 12 or higher, and sometimes a very large number, particularly in essentially infinitely repeating structures. The regular structures produced by the self-assembling fusion proteins may be produced by identical fusion proteins, such that the structure is homogenous with respect to the fusion protein "building blocks," or may be produced by a plurality of fusion proteins that differ from each other in terms of amino acid sequence, such that the structure is heterogeneous with respect to the fusion protein "building blocks." Where the structure is made up of a plurality of different fusion proteins of differing amino acid sequence, the number of different fusion proteins typically ranges from 2 to 4, usually from 2 to 3 and is often 2.

As mentioned above, the subject fusion proteins are capable of self-assembling under suitable conditions to produce regular structures. Suitable conditions are those conditions sufficient to provide for the self-assembly or association of the disparate fusion proteins into a regular structure. Typically, the conditions under which self-assembly of the subject fusion proteins occurs are physiologic conditions or other laboratory conditions under which the individual component proteins would be stable. By physiologic conditions is meant conditions found in living cell, e.g. a microbial, plant or animal cell. Typically, the conditions comprise an aqueous medium having a pH ranging from about 4 to 10 and usually from about 6 to 8, where the temperature ranges from about 4° C. to 35° C. However, it is understood that some proteins such as those from thermophilic microorganisms are stable under very extreme conditions and that structures from such stable components may have applications under such conditions.

The subject fusion proteins can be used to produce a variety of different regular structures. By "regular structure" is meant that the structure has a defined two- or three-dimensional configuration in space which is known. The structures produced by the self-assembly of the subject fusion proteins may be finite structures, such as nanoparticle shells, cages, double layer rings and the like. Where the structures are finite structures, they are typically nanostructures, having longest dimensions ranging in length from about 40 Å to 350 Å, usually from about 100 Å to 300 Å. Generally, these finite nanostructures have molecular weights ranging from about 200 kDa to more than 3,000 kDa and usually from about 300 kDa to 1,500 kDa. Alternatively, the subject fusion proteins may self-assemble into effectively infinitely repeating regular structures, such as two-dimensional layers, three-dimensional crystals; and filaments and tubes of indefinite length. In the subject fusion proteins, each oligomerization domain, e.g. naturally occurring protein component, serves as an oligomerization domain which provides for the association of the fusion proteins into the regular structure. As such, the relative orientations of the disparate components of the fusion protein are selected to provide for the desired regular structure upon self-assembly under suitable conditions. Accordingly, for any given fusion protein, the relative orientation of each component thereof is chosen based on the structure into which the fusion protein is designed to self-assemble. More specifically, the geometric relationship of the symmetry elements of the oligomerization domains of the subject fusion proteins are chosen based on the desired regular structure.

The symmetry elements of a given fusion protein are configured relative to each other in a marmer to provide for the overall symmetry required to produce the desired structure. As such, the geometry of the symmetry elements may be intersecting or non-intersecting, depending on the desired structure to be produced. Where the structure is a finite structure, the symmetry elements are generally intersecting. Where the structure is an infinite structure, the symmetry elements are generally non-intersecting, although if there are more than two symmetry elements, some pairs may also intersect.

Thus the fusion proteins can have a geometry of symmetry elements that gives rise to cage or shell structures upon self-assembly. These fusion proteins are generally proteins comprising two oligomerization domains, one of which is a protein that naturally associates into dimeric structures and one of which is a protein that naturally associates into a trimeric structures. The geometry of the symmetries of each of the components is such that they intersect. The angle of intersection varies depending on the specific structure to be formed, but generally ranges from about 50° to 60°, 30° to 40°, or 15° to 25°. Of particular interest are fusion proteins in which the angle is substantially the same as, or is, either 54.7, 35.3 or 20.9°. Specific examples of fusion protein geometrics suitable for the production of shells or cages can be found in Table 1, infra.

Fusion proteins are also provided that self-assemble into double-layer rings. These fusion proteins typically include two oligomerization domains, where the symmetry elements of the two oligomerization domains intersect. The angle between the symmetry elements generally ranges within 5° from the nearest integral fraction of 360° (i.e. 180°, 120°, 90°, 72°, 60°, 45°, etc.)

Generally, each oligomerization domain of these fusion proteins is a naturally occurring protein that is capable of associating with an identical protein to produce a dimeric structure. Specific examples of fusion protein geometries suitable for the production of double-layer rings can be found in Table 1, infra.

Also provided are fusion proteins that self-assemble into two-dimensional layers of infinite size, i.e. ordered protein layers that extend indefinitely in two dimensions. In this class of fusion proteins, the fusion proteins generally comprise either two or three oligomerization domains. Where the proteins comprise two oligomerization domains, they generally comprise a first oligomerization domain that is a naturally occurring protein which naturally assembles into trimeric structures and a second oligomerization domain that is a naturally occurring protein which naturally assembles into dimeric or trimeric structures. In these fusion proteins, the symmetry elements are configured such that they do not intersect. The angle formed between the non-intersecting symmetry elements is either 0 or 90°. Specific examples of fusion protein geometries suitable for the production of two-dimensional layers can be found in Table 1, infra.

Fusion proteins are also provided that self-assemble to produce three-dimensional crystals. In this class of fusion proteins, the fusion proteins generally comprise two oligomerization domains, where the two oligomerization domains may be naturally occurring proteins that naturally associate into dimeric or trimeric structures. In one embodiment, the fusion proteins comprise a first oligomerization domain that is a naturally occurring protein which naturally assembles into dimeric structures and a second oligomerization domain that is a naturally occurring protein which naturally assembles into trimeric structures. In a second embodiment, both the first and second oligomerization domains of the fusion protein are naturally occurring proteins that naturally associate into trimeric structures. The angles between the symmetry elements of these fusion proteins are non-intersecting, and generally range from about 65 to 75°, 50 to 60°, or 30 to 40°. Of particular interest are fusion proteins in which the angle is substantially the same as, or is, either 54.7, 35.3 or 70.5°. Specific examples of fusion protein geometries suitable for the production of three-dimensional crystals can be found in Table 1, infra.

Fusion proteins are also provided which self-assemble into helical filament and nanotube structures. For helical filaments, the fusion proteins generally comprise two oligomerization domains, where each of the oligomerization domains is a naturally occurring protein that assembles into dimeric structures. For the production of nanotube structures, the fusion proteins can consist of three oligomerization domains, each one of which is a protein that naturally assembles into dimeric structures. As with other fusion proteins that form structures of infinite length, the symmetry elements are non-intersecting. Furthermore, the symmetry elements of the various oligomerization domains intersect the cylindrical axis of the tube formed upon self-assembly of the fusion proteins in a perpendicular fashion. Specific examples of fusion proteins suitable for the production of filaments or tubes can be found in Table 1, infra.

TABLE 1

Rules for designing self-assembling protein architectures from dimeric and trimeric components*

| Symmetry | Construction† | Geometry of Symmetry Elements‡ |
|---|---|---|
| | | cages and shells |
| T | D-T | 2,3:54.7°, I |
| O§ | D-T | 2,3:35.3°, I |
| I | D-T | 2,3:20.9°, I |
| | | double-layer rings |
| $D_n$ | D-D | 2,2:180°/n, I |
| | | two-dimensional layers |
| p6¶ | D-T | 2,3:0°, N |
| p321 | D-T | 2,3:90°, N |
| p3 | T-T | 3,3:0°, N |
| | | three-dimensional layers |
| $I2_13$ | D-T | 2,3:54.7°, N |
| $P4_132$ or $P4_332$° | D-T | 2,3:54.7°, N |
| P23 | T-T | 3,3:70.5°, N |

TABLE 1-continued

Rules for designing self-assembling protein
architectures from dimeric and trimeric components*

| Symmetry | Construction† | Geometry of Symmetry Elements‡ |
|---|---|---|
| | | filaments of infinite length |
| helical | D-D | 2,2:any angle, N tubes of infinite length |
| p2** | D-D-D | 2,2,2:N,N,N, each intersecting the cylinder axis perpendicularly†† |

*The list is not exhaustive. Some designs that tend to give sterically impossible models are omitted.
†D and T refer to dimeric and trimeric structures, respectively. The order of connectivity within the protein chain is unimportant.
‡The first numbers indicate the types of symmetry elements involved. The angle formed between the symmetry elements is given, followed by I or N, for intersecting or non-intersecting.
§See FIG. 2a
¶See FIG. 2b
⌑The handedness of the space group depends on which symmetry axis passes on top.
**This is essentially a layer symmetry p2 rolled into a sheet
††One additional restriction arises from the continuity of the rolled up sheet Nucleic Acids Encoding the Fusion Proteins Also provided by the subject invention are nucleic acid compositions. By nucleic acid composition is meant a composition comprising a sequence of nucleotides having an open reading frame that encodes a fusion protein of the subject invention, as described supra. As such, the subject nucleic acid compositions at least comprise a nucleic acid sequence that encodes each of the oligomerization domains, where these sequences are generally joined by a sequence that encodes an amino acid sequence that is prone to form an alpha-helical configuration. Though the length of the subject nucleic acid compositions may vary greatly depending on the particular fusion protein that is encoded thereby, generally the subject nucleic acid compositions are at least about 200 bp long, usually at least about 400 bp long, and more usually at least about 600 bp long, where the subject nucleic acid compositions may be as long as 5.4 kbp or longer, but will usually not exceed about 2.7 kbp in length.

The subject nucleic acid compositions may be produced by standard methods of restriction enzyme cleavage, ligation and molecular cloning. One protocol for constructing the subject nucleic acid compositions includes the following steps. First, purified nucleic acid fragments containing desired component nucleotide sequences as well as extraneous sequences are cleaved with restriction endonucleases from initial sources, e.g. animal cell, plant cell or microbial or viral genomes. Fragments containing the desired nucleotide sequences are then separated from unwanted fragments of different size using conventional separation methods, e.g., by agarose gel electrophoresis. The desired fragments are excised from the gel and ligated together in the appropriate configuration so that a circular nucleic acid or plasmid containing the desired sequences, e.g. sequences corresponding to the various elements of the subject nucleic acid compositions, as described above, is produced. Where desired, the circular molecules so constructed are then amplified in a prokaryotic host, e.g. *E. coli*. The procedures of cleavage, plasmid construction, cell transformation and plasmid production involved in these steps are well known to one skilled in the art and the enzymes required for restriction and ligation are available commercially. (See, for example, R. Wu, Ed., Methods in Enzymology, Vol. 68, Academic Press, N.Y. (1979); T. Maniatis, E. F. Fritsch and J. Sambrook, Molecular Cloning: A Laboratory Manual, Cold Spring Harbor Laboratory Press, Cold Spring Harbor, N.Y. (1982); Catalog 1982–83, New England Biolabs, Inc.; Catalog 1982–83, Bethesda Research Laboratories, Inc.

The above nucleic acid compositions find use in the preparation of the subject fusion proteins.

Methods of Preparing the Subject Fusion Proteins

The subject fusion proteins are obtained by expressing a recombinant gene encoding the fusion proteins, such as the polynucleotide compositions described above, in a suitable host. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be derived from a variety of sources.

Expression vectors generally have convenient restriction sites located near the promoter sequence to provide for the insertion of nucleic acid sequences encoding heterologous proteins. A selectable marker operative in the expression host may be present. Expression cassettes may be prepared comprising a transcription initiation region, the region encoding the fusion protein, and a transcriptional termination region. After introduction of the DNA, the cells containing the construct may be selected by means of a selectable marker, the cells expanded and then used for expression.

The proteins may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the proteins in eukaryotic cells, where the encoded protein will benefit from native folding and post-translational modifications.

Where desired, the protein may be purified following its expression to produce a purified protein comprising composition. Any convenient protein purification procedures may be employed, where suitable protein purification methodologies are described in Guide to Protein Purification, (Deuthser ed.) (Academic Press, 1990). For example, a lysate may be prepared from the original source, e.g. the expression host expressing the protein, and purified using HPLC, exclusion chromatography, gel electrophoresis, affinity chromatography, and the like.

Preparation of Regular Structures

The subject fusion proteins find use in the production of various types of regular structures, i.e. structures of defined and predictable geometry. Specifically, the subject fusion proteins find use in the preparation nanoparticle shells and cages, two-dimensional crystalline layers, three-dimensional crystalline layers, helical filaments and nanotubes, etc.

To prepare regular structures from the subject fusion proteins, the fusion proteins are generally combined under conditions sufficient for self-assembly of the fusion proteins into the desired regular structure to occur. Generally, the conditions that promote self-assembly are physiologic conditions, as mentioned above. The concentration of the fusion protein in the medium must be sufficiently high such that self-assembly into the desired structure occurs. Typically, the fusion protein concentration is at least about 0.05 mg/ml and more usually at least about 0.25 mg/ml.

In many embodiments, such as in the production of finite regular structures, the structures are assembled from a plurality of identical fusion proteins, i.e. they are homogenous with respect to the fusion protein. In such embodiments, preparation of the fusion protein (e.g. expression of a nucleic acid encoding the protein) may occur in the same medium as assembly of the structure, e.g. in the host cell used to express the fusion protein. In other embodiments where the structure is assembled from two or more distinct fusion proteins, i.e. it is heterogeneous with respect to the nature of the fusion protein building block, the opportunity arises to express the disparate types of fusion protein building blocks in different hosts, purify the fusion proteins and then combine the fusion proteins under conditions sufficient for self assembly of the structure to occur. Such a protocol is attractive where one is producing infinite structures.

Utility

The regular structures produced by the self assembly of the subject fusion proteins find use in a variety of different applications. As mentioned above, structures can be assembled that resemble either an open cage, a closed shell or a relatively compact ball. Hollow structures find use in drug or gene delivery; for stabilizing, shielding or sequestering other molecules in their interior volumes; and the like. More compact structures find use in the presentation of multiple antigens, or other optically or electronically active chemical groups. The subject fusion proteins can also be employed to assemble two-dimensional layers, where such ordered protein layers find use as biological coatings, sensors, detectors, molecular sieves, and the like. Where the fusion proteins are employed to produce three-dimensional layers, the resultant structures find use as molecular sieves, biological matrices, carriers for crystallizing small molecules, and the like.

Kits

Also provided are kits for use in producing the subject fusion proteins and self-assembled regular structures. The subject kits at least include a nucleic acid composition that encodes a fusion protein, where the nucleic acid is typically present on a vector. The kits may further include expression hosts suitable for expressing the subject fusion proteins. Also provided in the kits may be other reagents useful for producing the subject fusion proteins, e.g. buffers, growth mediums, enzymes, selection reagents, and the like.

The following examples are offered by way of illustration and not by way of limitation.

EXPERIMENTAL

EXAMPLE I

Laboratory Production of a Protein Cage

Figure 1:
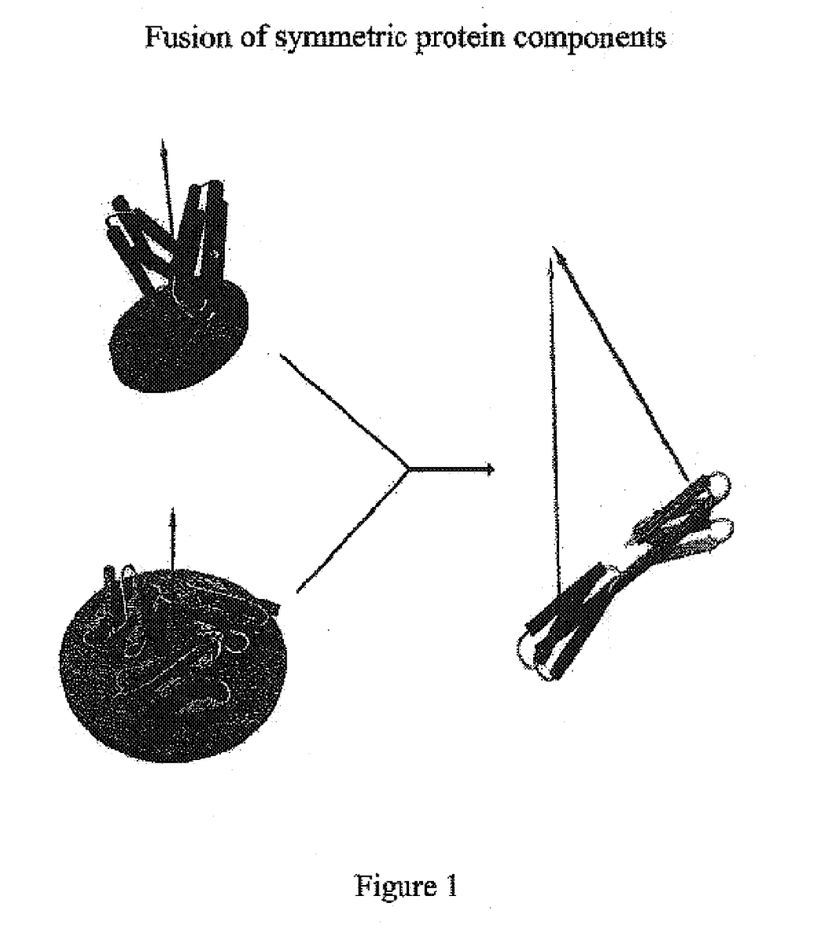
FIG. 1. A general strategy for constructing a chimeric self-assembling protein from two oligomeric proteins. The structures of the component proteins are known; one begins and one ends in an alpha helix. The linker is also helical. The component proteins and linker are chosen so that the combined symmetry elements meet prescribed rules for various self-assembling architectures.

Those dimeric and trimeric protein structures (i.e. proteins that naturally associate into dimeric and trimeric structures, respectively) that begin or end in alpha helices were identified in the Protein Databank (Abola et al., Meth. Enzymol. (1997)277:566–571) Using a computer program, dimers and trimers were connected pairwise by a continuous, intervening alpha helical segment (FIG. 1). For each pair of components, the length of the helical linker was incremented from 2 to 30 residues. For each model choice, the symmetry elements belonging to the dimeric and trimeric components were examined computationally to see if they nearly intersected and, if so, at what angle. Those designs for which the intersection angle nearly matched one of the target angles for cubic symmetry (Table 1) were checked for steric clashes in the complete assembly. Several promising designs were obtained.

The first design for which clones could be obtained of both components was a tetrahedral cage constructed as a fusion of the trimeric bromoperoxidase (Hecht, et al. Nature Struc. Biol. (1994) 1:532–537 (kindly provided by H. J. Hecht)) and the dimeric M1 matrix protein of influenza virus (Sha, et al., Acta. Cryst. D. (1997) 53:458–460) (kindly provided by Ming Luo). The helical linker was 9 residues in length. According to the design, the tetrahedral cage was expected to be approximately 90 Å on an edge, or about 150 Å in diameter. The central cavity would hold a sphere of radius 40 Å.

Figure 3A:
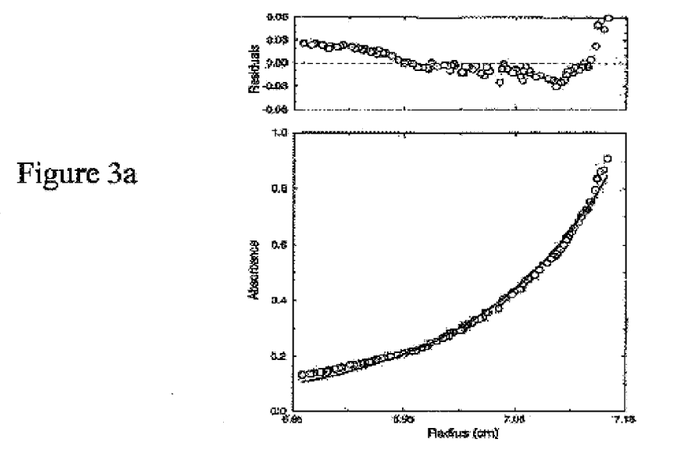
Figure 3B:
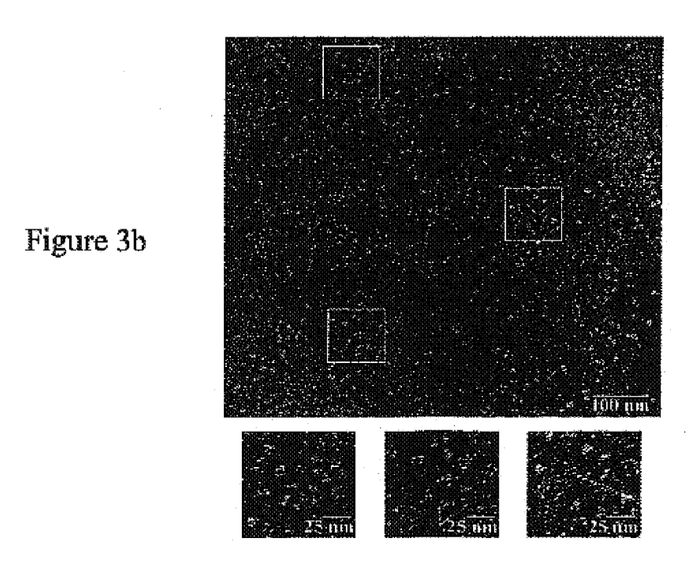
Figure 4:
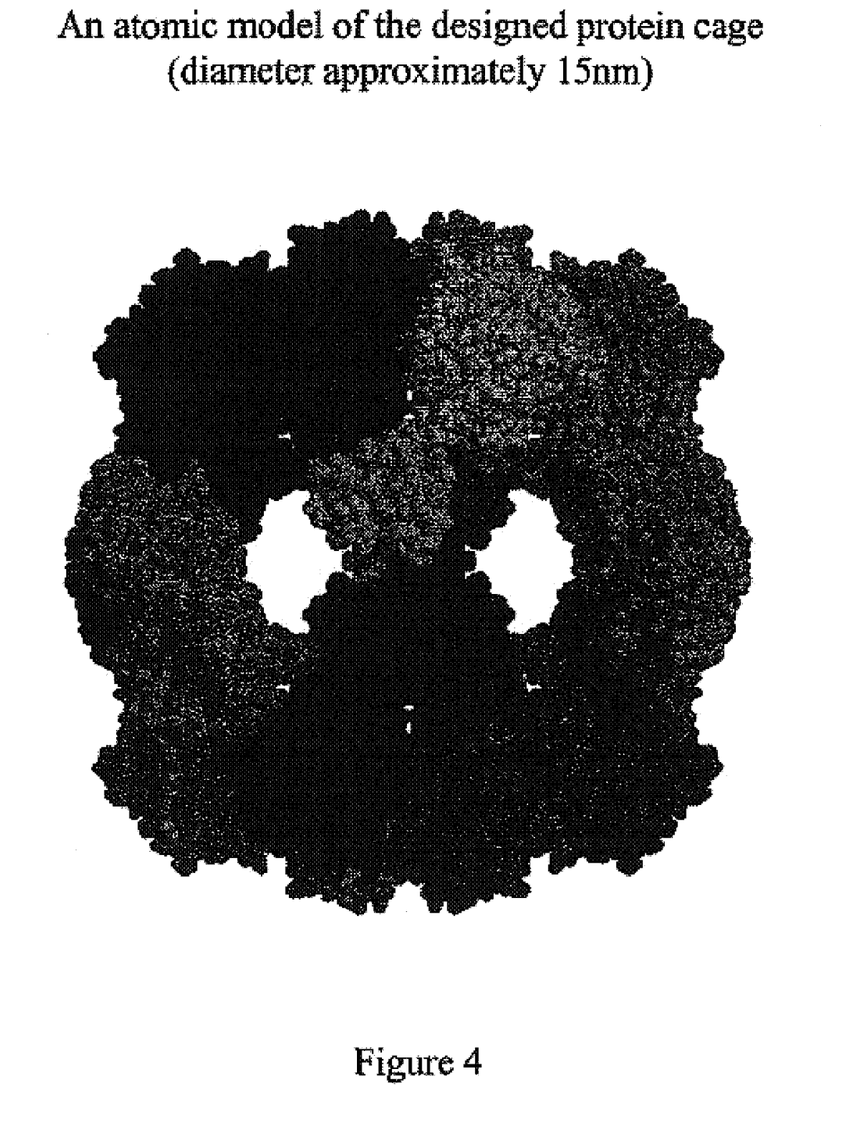
FIG. 4. The structure of a tetrahedral protein cage which assembles by design from 12 copies of a 50 kDa engineered protein. The particle diameter is approximately 150 Å. Separate protein chains are colored individually.

The hybrid 50 kDa protein was engineered, expressed, and purified from *E. coli*. The protein behaved well in solution, remaining soluble at concentrations as high as 20 mg/ml. A variety of experimental methods were used to demonstrate that the designed protein self-assembles as designed (FIG. 3). Although all experiments were consistent with self-assembly, shape-sensitive methods such as light scattering and sedimentation velocity could not be easily converted to a molecular weight. Equilibrium sedimentation gave a shape-independent molecular weight of 540 kDa, which corresponds to slightly less than 12 subunits. This minor discrepancy might result from sample impurity or from equilibrium with small amounts of partially assembled species. Negatively stained electron micrographs show a field of triangular objects of the anticipated size. These are presumably footprints of the roughly triangular tetrahedral faces. FIG. 4 shows a space filling model of the designed structure.

EXAMPLE II

Laboratory Production of a Self-Assembling Protein Filament

Figure 5A:
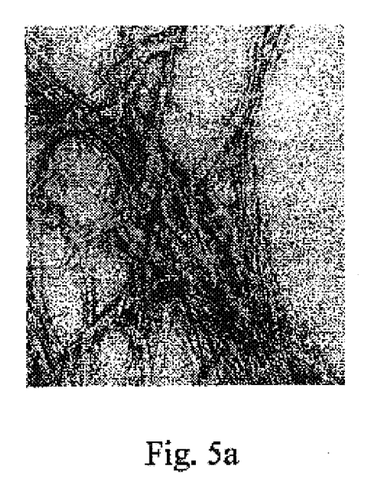
FIG. 5a shows a network of filaments and FIG. 5b shows a bundle of filaments, according to the subject invention.
Figure 5B:
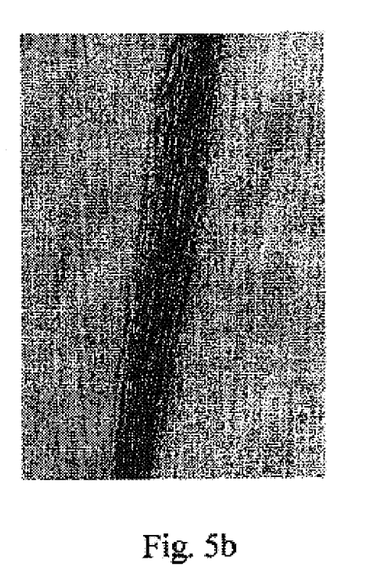
Figure 6:
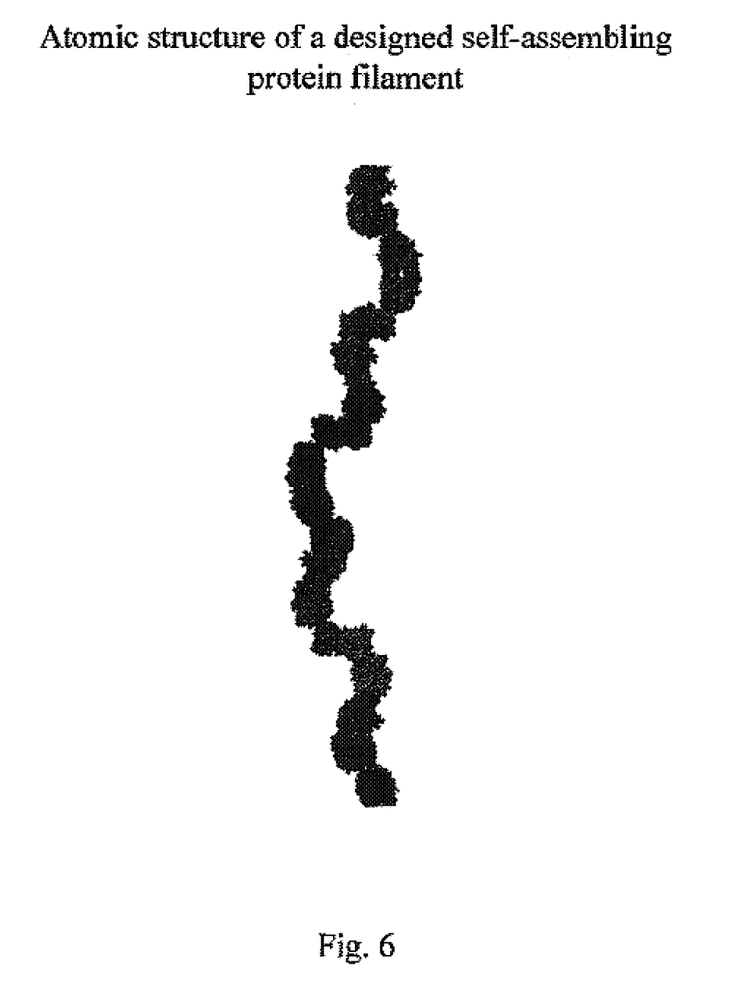
FIG. 6 shows a space-filling diagram of the filament structure, with separate protein molecules in different colors.

Using the same computer based search procedure as described above, a fusion protein intended to self-assemble into roughly linear filaments was designed as a fusion between two dimeric components. The two component proteins are carboxylesterase from *Pseudomonas fluorescens* (PDB code 1auo) and influenza virus matrix protein (PDB code 1aa7). The linker is 5 amino acid residues. The molecular weight of the fusion protein is 41.4 kDa. According to the design principles described here, the fusion protein was expected to self-assemble into filaments of indefinite length with a width of approximately 30 Å. The designed fusion protein was cloned, expressed, and purified from an *E. coli* expression system. The purified protein was examined by electron microscopy which showed filaments with the expected dimensions. FIG. 5a shows a network of such filaments and FIG. 5b shows a bundle of filaments. FIG. 6 shows a space-filling diagram of the filament structure, with separate protein molecules in different colors.

EXAMPLE III

Enumeration of Self-Assembled Structures

A. Nanoparticle Shells and Cages

Figure 2A:
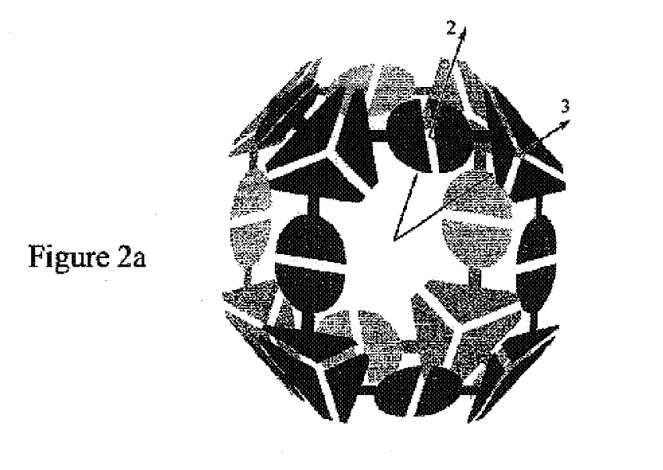

The finite structures are based on the well-known point group symmetries. Double ring structures with dihedral symmetry can be assembled with hybrid proteins created from two dimeric components (Table 1). Symmetric cage-like assemblies are also of interest. These structures are based on the cubic point symmetries: tetrahedral, octahedral, and icosahedral. These cages or shells are designed to assemble respectively, from 12, 24, and 60 copies of a designed protein (FIG. 2a). All of the cubic symmetries, even icosahedral, can be produced by connecting a naturally dimeric protein to a trimeric protein by a rigid linker that forces the two-fold and three-fold symmetry axes of the two components to intersect. In fact, the only distinction between the tetrahedral, octahedral, and icosahedral designs is the angle formed by the two symmetry axes (Table 1).

Cubically symmetric shells can also be produced from other combinations of individual symmetry elements, using (cyclic) tetramers and pentamers for example. But these components are very rare among natural proteins. This presents no problem, because relatively abundant dimers and trimers are sufficient to construct all of the architectures discussed here.

Depending on the geometric details, a particular finite assembly may resemble either an open cage, a closed shell, or a relatively compact ball. Hollow structures may be useful for delivering drugs or genes, or for stabilizing, shielding, or sequestering other molecules in their interior volumes. More compact structures might be useful for presenting multiple copies of antigens or other optically or electronically active chemical groups on their surfaces.

Symmetric carbon-based shells, such as fullerenes, have been synthesized and widely studied. The protein shells discussed here would typically be larger than fullerene shells by a factor of 10 to 40 in linear dimension. There has been considerable interest in modifying cages. Here, the chemical diversity and ease of genetic manipulation of proteins should offer special advantages. For example, individual amino acids or additional protein domains could be incorporated easily to carry enzymatic activity, ligands for specific receptors, sites for specific chemical modification, or antigenic epitopes. Designs might also incorporate proteins with metal or ligand-sensitive conformations, leading to materials that would assemble or disassemble in response to a signal.

Regular geometric cages have also been designed with nucleic acids. There, the desired connectivity is promoted by using a mixture of several components (e.g. one for each edge of the object), each of which is complimentary to the components in adjoining edges. In contrast, the protein-based strategy presented here takes special advantage of the symmetry and equivalence of the building blocks, although a variation involving two component systems is discussed later.

B. Two-dimensional Crystalline Layers

Figure 2B:
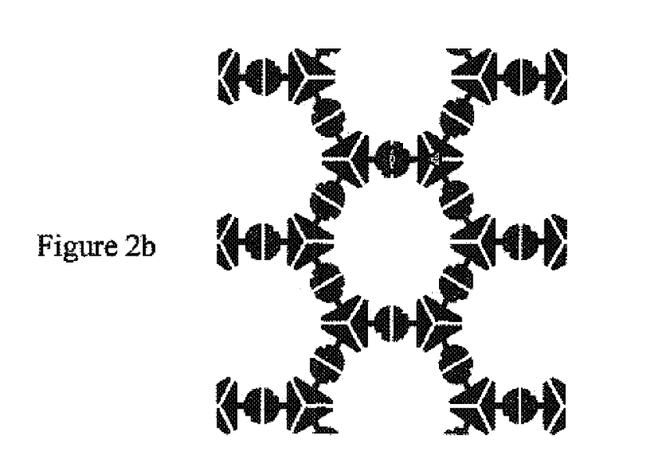

The same design principles can be applied to make ordered protein layers that extend indefinitely in two dimensions. These structures are based on the two-dimensional layer symmetries. The key feature of the infinite assemblies is that the symmetry axes must be designed so as to not intersect. Different combinations of individual symmetry elements lead to a variety of symmetries (Table 1). Two of these, layer symmetries p6 and p321, can be constructed by fusing a dimer to a trimer. Both are essentially hexagonal networks, but the top and bottom surfaces of the former design differ, while the two surfaces of the latter design are identical (FIG. 2b). Other layer symmetries not specifically listed in Table 1 can be realized by including a tetramer or hexamer as a component of the fusion protein. In all cases, the separation between the non-intersecting symmetry elements dictates the repeat length or unit cell of the layer.

Well ordered molecular layers may have applications as biological coatings, sensors, or detectors (Aizawa, et al. Sensors and Actuators B, (1998) 52:204–211). Layers with large pores could be useful as molecular sieves. Porous materials have been fabricated from silicates and more recently from metal sulfides and metal phosphates, but it has been difficult to exceed a pore diameter of roughly 14 Å. The protein-based materials described here could have pore sizes in the 50 Å to 200 Å range. Less regular molecular networks have been produced using mixtures of nucleic acids.

Equally simple designs can be used to produce three-dimensional crystalline networks of proteins. Depending on the geometry (Table 1), three different crystalline space groups, $I2_13$, $P4_132$, and $P4_332$ can be generated by fusing a dimeric and a trimeric protein. These three-dimensional materials could also be designed to have large pore diameters. Cubic symmetry makes the structures isotropic, and therefore not especially deformable in any particular direction. Consequently, one may expect them to be relatively rigid, despite their porosity. Owing to their precisely defined pore sizes, these materials could be especially useful as molecular sieves. They may also be usefull as biological matrices or as carriers for crystallizing other molecules small enough to fit within the interstitial spaces.

C. Helical Filaments and Nanotubes

In principle, the present method of construction can produce extended linear structures of various types. For example, a simple helical filament is formed in general by connecting two dimeric components. The resulting helix is symmetric in a way that makes the two ends indistinguishable. As a special case, a linear filament is generated when the two-fold symmetry elements are parallel. As another variation, a structure can be designed so that successive turns of the helical filament make contact. The result would be a hollow tube which might bend or deform easily, since the contacts between successive rings would be non-specific.

A fundamentally different kind of tube can be designed by connecting three dimeric components in sequence. The resulting architecture is based on a connected layer of molecules with p2 symmetry, rolled into a cylinder. Owing to the connectivity of the cylindrical molecular surface, structures based on this design might be especially rigid.

Methods have already been developed to prepare carbon-based nanotubes resembling rolled up graphite sheets. Slightly larger tubes have also been prepared from short synthetic circular polypeptides which stack upon each other to form a cylindrical beta sheet. The protein-based tubes described here would be considerably larger in diameter, perhaps 100 to 400 Å. In addition, it should be straightforward to chemically modify such protein tubes, possibly at interior positions, to produce novel materials with unusual electronic or optical properties.

EXAMPLE IV

Binary Mixtures

All of the effectively infinite architectures described above suffer from a possible experimental obstacle: due to aggregation, it may be difficult to produce the engineered proteins in bacteria using recombinant methods. We propose a general solution to this possible problem, which is to design the infinite architectures as two components. Each of the two components would be connected in a defined fashion to one half of a heterodimeric protein pair, which would drive the association of the separate components. The two components would be expressed and purified from separate bacteria and then mixed. As before, the structure of the heterodimer must be known. Aside from these requirements, the strategy is completely general and applies equally well to all the architectures.

It is evident from the above results and discussion the subject invention provides powerful tools and methodologies for producing ordered structures from naturally occurring proteins. The fusion proteins of the subject invention can be readily produced and then self-assembled into a variety of different structures which find use in a plurality of different applications. As such, the subject invention represents a significant contribution to the field.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A fusion protein of at least two oligomerization domains comprising a first oligomerization domain that naturally associates into homodimeric structures and a second oligomerization domain that naturally associates into homotrimeric structures rigidly linked to each other, wherein said fusion protein is capable of self-assembling with additional fusion proteins to produce a regular structure.

2. The fusion protein according to claim 1, wherein said at least two oligomerization domains are derived from naturally occurring proteins.

3. The fusion protein according to claim 1, wherein said fusion protein has a geometry of symmetry that is intersecting.

4. The fusion protein according to claim 1, wherein said at least two oligomerization domains are rigidly linked to each other by a linking group.

5. The fusion protein according to claim 1, wherein said fusion protein has a geometry of symmetry that is non-intersecting.

6. The fusion protein according to claim 3, wherein said geometry of symmetry has an angle of intersection chosen from an angle that is:
    (a) 54.7°;
    (b) 35.3°; and
    (c) 20.9°.

7. The fusion protein according to claim 6, wherein said geometry of symmetry has an angle of intersection that is chosen from an angle that is:
    (a) 54.7°; and
    (b) 35.3°.

8. A fusion protein of at least two oligomerization domains comprising a first oligomerization domain that naturally associates into homodimeric structures and a second oligomerization domain that naturally associates into homotrimeric structures derived from naturally occurring proteins rigidly linked to each other by an alpha helical linking group, wherein said fusion protein is capable of self-assembling with additional fusion proteins to produce a regular structure.

9. The fusion protein according to claim 8, wherein said fusion protein has a geometry of symmetry that is intersecting.

10. The fusion protein according to claim 9, wherein said geometry of symmetry has an angle of intersection chosen from an angle that is, or is:
    (a) 54.7°;
    (b) 35.3°; and
    (c) 20.9°.

11. The fusion protein according to claim 8, wherein said fusion protein has a geometry of symmetry that is non-intersecting.

12. The fusion protein according to claim 10, wherein said geometry of symmetry has an angle of intersection that is chosen from an angle that is:
    (a) 54.7; and
    (b) 35.3°.

13. A regular structure produced by the self-assembly of a plurality of fusion proteins according to claim 1.

14. The regular structure according to claim 13, wherein said structure is homogenous with respect to its fusion protein components.

15. The regular structure according to claim 13, wherein said structure is heterogeneous with respect to its fusion protein components.

16. The regular structure according to claim 15, wherein said structure comprises two different types of fusion proteins.

17. The regular structure according to claim 13, wherein said regular structure is selected from the group consisting of: cages, shells, two-dimensional layers, and three-dimensional crystals.

18. A method of producing a regular structure, said method comprising:
    producing a plurality of fusion proteins according to claim 1; and
    combining said plurality of fusion proteins under conditions sufficient for said regular structure to form.

19. The method according to claim 18, wherein said conditions are physiologic conditions or other laboratory conditions under which the component oligomerization domains would be stable.

20. The method according to claim 18, wherein said producing and combining steps occur in the same reaction medium.

21. The method avoiding to claim 18, wherein said producing and combining steps occur in separate media.

22. The fusion protein according to claim 1, wherein said regular structure comprises 12 or more copies of said fusion protein arranged in a symmetrical fashion.

23. The fusion protein according to claim 8, wherein said regular structure comprises 12 or more copies of said fusion protein arranged in a symmetrical fashion.

24. A regular structure produced by the self-assembly of a plurality of fusion proteins according to claim 23.

25. A method of producing a regular structure, said method comprising:
    producing a plurality of fusion proteins according to claim 23; and
    combining said plurality of fusion proteins under conditions sufficient for said regular structure to form.

26. The fusion protein according to claim 1, wherein said oligomerization domain of said fusion protein has a molecular weight of about 2 kDa to about 100 kDa.

27. The fusion protein according to claim 26, wherein said oligomerization domain of said fusion protein has a molecular weight of about 2 kDa to about 10 kDa.

* * * * *

UNITED STATES PATENT AND TRADEMARK OFFICE
CERTIFICATE OF CORRECTION

PATENT NO. : 6,756,039 B1
DATED : June 29, 2004
INVENTOR(S) : Todd O. Yeates et al.

It is certified that error appears in the above-identified patent and that said Letters Patent is hereby corrected as shown below:

Column 13,
Line 58, the words "is, or" after the word "that" and before the word "is" should be removed.

Signed and Sealed this

Sixteenth Day of November, 2004

JON W. DUDAS
*Director of the United States Patent and Trademark Office*